(12) United States Patent
Lloyd et al.

(10) Patent No.: US 6,863,693 B2
(45) Date of Patent: Mar. 8, 2005

(54) PHOSPHOLIPID-COATED IMPLANTS

(75) Inventors: Andrew W. Lloyd, Brighton (GB); Matteo Santin, Brighton (GB); Stephen P. Denyer, Brighton (GB); William Rhys-Williams, Brighton (GB); William G. Love, Brighton (GB)

(73) Assignees: Destiny Pharma Limited, Brighton (GB); University of Brighton, Brighton (GB)

( * ) Notice: Subject to any disclaimer, the term of this patent is extended or adjusted under 35 U.S.C. 154(b) by 122 days.

(21) Appl. No.: 10/084,677

(22) Filed: Feb. 28, 2002

(65) Prior Publication Data

US 2002/0165617 A1 Nov. 7, 2002

Related U.S. Application Data

(63) Continuation-in-part of application No. PCT/GB00/03290, filed on Aug. 29, 2000.

(30) Foreign Application Priority Data

Aug. 31, 1999 (GB) .............................................. 9920547

(51) Int. Cl.[7] .................................................. A61F 2/28
(52) U.S. Cl. .................................................. 623/23.57
(58) Field of Search ........................... 623/23.57, 23.6, 623/23.76; 427/2.26; 424/423

(56) References Cited

U.S. PATENT DOCUMENTS

| 4,749,585 | A | | 6/1988 | Greco et al. |
|---|---|---|---|---|
| 5,342,621 | A | | 8/1994 | Eury |
| 5,722,984 | A | | 3/1998 | Fischell et al. |
| 5,755,788 | A | * | 5/1998 | Strauss ........................ 623/1.1 |
| 5,782,908 | A | * | 7/1998 | Cahalan et al. ............. 623/1.13 |
| 5,968,091 | A | * | 10/1999 | Pinchuk et al. ............. 623/1.16 |
| 6,231,590 | B1 | * | 5/2001 | Slaikeu et al. .............. 606/200 |
| 6,254,634 | B1 | * | 7/2001 | Anderson et al. ........... 623/1.42 |
| 6,290,718 | B1 | * | 9/2001 | Grooms et al. ............. 623/1.15 |
| 6,416,549 | B1 | * | 7/2002 | Chinn et al. ................ 623/2.36 |
| 2001/0039432 | A1 | * | 11/2001 | Whitcher et al. ........... 606/200 |
| 2001/0047202 | A1 | * | 11/2001 | Slaikeu et al. .............. 623/1.46 |
| 2002/0198599 | A1 | * | 12/2002 | Haldimann ............... 623/17.16 |

FOREIGN PATENT DOCUMENTS

| EP | 0 479 582 A1 | 4/1992 |
|---|---|---|
| EP | 0 806 212 A1 | 11/1997 |
| EP | 0 923 953 | 6/1999 |
| EP | 0 923 953 A2 | 6/1999 |
| JP | 3-294221 | 12/1991 |
| WO | WO 91/00745 A1 | 1/1991 |

OTHER PUBLICATIONS

Radin et al. "Calcium phosphate ceramic coatings as carriers of vancomycin", Biomaterials, GB, Elsevier Science Publishers BV., Barking, vol. 18, No. 11, Jun. 1, 1997 pp. 777–782.

(List continued on next page.)

Primary Examiner—Eduardo C. Robert
(74) Attorney, Agent, or Firm—Browdy and Neimark, P.L.L.C.

(57) ABSTRACT

A prosthesis or implant has a surface carrying a coating comprising at least one phospholipid at a concentration to improve osteointegration. A method of making such a prosthesis or implant and a kit comprising a prosthesis or implant is also described.

18 Claims, 9 Drawing Sheets

OTHER PUBLICATIONS

Williams et al. "Fabrication and characterization of dipalmitoylphosphatidylcholine–at tracting elastomeric material for joint replacements", Biomaterials, GB, Elsevier Science Publishers BV., Barking, vol. 16, No. 15, Oct. 1, 1995, pp. 1169–1174.

Williams et al., "Fabrication and Charaterization of Dipalmitoylphosphatidylcholine–attracting Elastomeric Material for Joint Replacements", *Biomaterials*, 1995, pp. 1169–1174, vol. 16, No. 15.

Vogel, "Calcium Phosphate Solid Phase Induction by Dioleoylphosphatidate Liposomes", *Journal of Colloid and Interface Science*, May 1986, pp. 152–159, vol. 111, No. 1.

Søballe et al., "Calcium Hydroxyapatite in Total Joint Anthroplasty", in *Human Biomaterial Applications*, New Jersey: Humana Press Inc., 1996, pp. 137–167.

Skrtic et al., "Membrane–Mediated Precipitation of Calcium Phosphate in Model Liposomes with Matrix Vesicle–like Lipid Composition", *Bone and Mineral*, 1992, pp. 109–119, vol. 16.

Revell, "Tissue Reactions to Joint Prostheses and the Products of Wear and Corrosion", *Current Topics PathologyU, 1982, pp. 73–102, vol. 71.*

Radin et al., "Calcium Phosphate Ceramic Coatings as Carriers of Vancomycin", *Biomaterials*, 1997, pp. 777–782, vol. 18.

Radin et al., "Effect of Serum Proteins on Solution–Induced Surface Transformations of Bioactive Ceramics", *J. Biomedical Materials Research*, 1996, pp. 273–279, vol. 30.

Lewis, "Properties of Acrylic Bone Cement: State of the Art Review", *J. Biomed. Mater. Res.*, 1997, pp. 155–182, vol. 38.

Heywood et al., "An Ultrastructural Study of Calcium Phosphate Formation in Multilamellar Liposome Suspensions", *Calcif Tissue Int*, 1987, pp. 192–201, vol. 41.

Eanes et al., "Calcium Phosphate Formation in Aqueous Suspensions of multilamellar Liposomes", *Calcif Tissue Int*, 1984, pp. 421–430, vol. 36.

Eanes et al., "Calcium Phosphate Precipitation in Aqueous Suspensions of Phosphatidylserine–Containing Anionic Liposomes", *Calcif Tissue Int*, 1987, pp. 43–48, vol. 40.

Eanes et al., "Liposome–Mediated Calcium Phosphate Formation in Metastable Solutions", *Calcif Tissue Int*, 1985, pp. 390–394, vol. 37.

Dhert, "Retrieval Studies on Calcium Phosphate–Coated Implants", *Medical Progress through Technology*, 1994, pp. 143–154, vol. 20.

P.P. Anthony et al., "Localised Endosteal Bone Lysis in Relation to the Femoral Components of Cemented Total Hip Athroplasties", *J. Bone Jt. Surg.*, 1990, pp. 971–979, vol. 72B.

* cited by examiner

Crystalline structures associated with lamellar structures

Calcium phosphate deposition on area coated with 222?m/mL formulation

Calcium phosphate deposition on area coated with 444?m/mL formulation

Ti-300Pore implant

Calcium phosphate deposition on area coated with 444 ?m/mL formulation

Ti-300Pore implant

Smooth surface of implant

Roughness of Ti-Pore300 surface

Calcium phosphate deposition on area coated with 444 ?m/mL formulation

Ti-300Pore implant

Ti-Pore300-HA implant

Calcium phosphate deposition on area coated with formulation

PHOSPHOLIPID-COATED IMPLANTS

This is a continuation of co-pending parent International application No. PCT/GB00/03290, filed Aug. 29, 2000.

BACKGROUND

The invention relates to prostheses or implants having a surface modification which improves the process of osteointegration. The invention also relates to methods for making such prostheses or implants and prosthetic or implant kits.

A major unresolved clinical problem in the management of orthopaedic conditions is the ability to implant orthopaedic prostheses, which achieve permanent fixation to surrounding bone. Presently, metal devices, whether cemented or non-cemented, show only poor osteointegration with a finite lifetime before loosening; porous ceramic coatings provide improvements but do not offer complete resolution[1]. There is considerable scope for improvement of orthopaedic implants, particularly in development of uncemented devices, which aim to improve osteointegration between implant and bone.

Cemented prostheses suffer from problems associated with thermal and chemical bone necrosis, cement shrinkage and stiffness mismatch, weak-link zones at {bone:cement:implant} interfaces and cement particles causing inflammation and bone erosion[2,3,4]. Uncemented prostheses were developed to overcome the problems associated with cement, however the clinical outcomes of these systems have been below expectation; the main problems being associated with failure of the bone:implant interface and osteolysis (in common with cemented systems)[5].

The outcome of surgery to install the implant is heavily dependent upon how the implant interacts with the host both in acute and chronic phases of healing. During the acute phase the inflammatory response is directly related to the surgical intervention. However the implant characteristics and its proximity to the bone come into play, fundamentally influencing the degree of osteointegration and therefore the longevity of the implant. Although not fully understood, the implant surface is thought to play an important role in osteointegration. Therefore the positioning of a biomaterial with a physical ultra-structure capable of forming a matrix or a scaffold for osteogenic cell attachment between the {bone:implant} interface may be advantageous in promoting osteointegration. Critical factors influencing the success of such biomaterials include biocompatibility, cellular adhesion, physical ultra-structure, and degradation,(related to residence time of the system).

Metals (e.g. titanium), ceramics (e.g. hydroxyapatite, bioglasses), and polymers (e.g. polyethylene oxide) are the biomaterials most frequently used as prosthetic alternatives to natural bone. These materials may be considered to be osteoconductive since they appear to offer acceptable support for cell attachment, growth and vascularisation. Beyond osteoconductivity, however, the principal properties demanded of these materials are mechanical strength and osteointegration. In particular, osteointegration, defined as a "direct structural and functional connection between ordered living bone and the surface of a load-carrying implant", is the major characteristic which ensures good long-term prosthesis functionality. In the case of titanium, hydroxyapatite and bioactive glass implants, mineralised bone is rarely deposited closer than 100 to 500 nm from the material surface; ultrastructural examination reveals an electron-dense zone interspersed between the mineralised tissue of the regenerating bone and the material surface. In this region, an interfacial layer of randomly distributed collagen filaments and proteoglycan exists; matrix mineralisation only takes place at the level of ordered collagen bundles.

Previous reports in the literature have reported the use of liposomal systems to investigate the role of matrix vesicles in bone growth. These matrix vesicles are thought to be the initial site of calcium phosphate precipitation in vitro[6]. Liposomes composed of phosphatidylcholine: dicetylphosphate: cholesterol (7:2:1 molar ratio) and an ionophore were used to demonstrate the transport of calcium into the liposomes and the formation of hydroxyapatite[7,8]. It was also demonstrated that no calcium phosphate was produced in these liposomes in the absence of an ionophore[9]. A decrease in the amount of free calcium in the buffer of approximately 0.2 mM or 9% of the initial calcium concentration within a 6-hour time period in liposomes containing dicetylphosphate was reported[7,10].

There is no evidence in the literature of the association of phospholipids with surfaces with the intention of precipitating calcium phosphate onto the surface. European Patent Number EP 0806212 refers to a technology to precipitate calcium phosphate onto the surface of an implantable device and lists the co-precipitation of biologically active substances onto the surface during the manufacture of the coating. No mention is given for the co-precipitation of calcium phosphate and phospholipids, no information is supplied as to their function and no contribution is claimed for an increase in the rate of precipitation. Japanese patent number JP 3294221 refers to the coating of ceramics with phospholipids and drug molecules. The phospholipids form liposomes containing the drug and appear to be entrapped within the holes in the ceramics. The stated purpose of the phospholipids is to prevent the infection of implanted artificial teeth by acting as a depot or slow release system for the drug molecule and no claim appears to be made for improving osteointegration of said artificial teeth. European Patent number EP0479582 refers to the use of antibiotic-containing liposomes combined with hydroxyapatite and collagen and placed into the area of resorbed jawbone to generate new bone tissue. No other claims are made with regards to any properties attributed to the presence of the phospholipids other than as carriers for the antibiotic. U.S. Pat. No. 5,755,788 describes the binding of liposomes to the surface of prostheses and implants which are designed to resist thrombosis development in the body.

It is an object of the invention to provide an improved prosthesis or implant which is susceptible of improved osteointegration or implant in vivo.

STATEMENTS OF INVENTION

The invention is based on the discovery that a coating of a phospholipid-type material on a surface can induce or enhance the precipitation on to that surface of calcium phosphate from a simulated body fluid.

Thus the invention provides in one aspect a prosthesis or implant having a surface carrying a coating comprising at least one phospholipid at a concentration to improve osteointegration. Other aspects of the invention are defined in the claims. "Osteointegration" is defined above.

The invention is mainly concerned with orthopaedic and load-bearing prostheses, for it is with these that osteointegration is of particular importance. The prosthesis or implant is generally a metal (e.g. titanium), a ceramic (e.g. hydroxyapatite or bioglas), or an organic polymer (e.g. polyethylene). These are in general osteoconductive rather than bioactive materials. The surface which carries a phospholipid coating may be the whole surface of the prosthesis or implant, but is more usually a part of the surface, particularly the part that is likely to be subjected to mechanical stress in vivo. The surface may be smooth, porous or made rough as well known in the art to provide an improved mechanical key for osteointegration. The prosthesis or implant ideally needs to be sterile, and one method by which this may conveniently be achieved by sterilising the device and then applying the phospholipid coating under sterile conditions.

Phospholipid is a term of art which defined a group of phosphate-containing lipids including the major structural lipids of most cellular membranes e.g. phosphatidyl phospholipids and sphingomyelins. Preferred phospholipids are those carrying a negative charge, including phosphatidylserine and phosphatidylinositol. These negatively charged phospholipids are believed to preferentially bind calcium in vivo, and phosphatidylserine is known to bind phosphate also. Such phospholipids are not themselves apt to form liposomes on mixing with water.

The phospholipid may be provided either as a solution in an organic solvent, or alternatively as a liposomal or other suspension in an aqueous fluid. The coating may comprise a phospholipid suspension which may be lyophilised or otherwise dried on the surface. As noted, the formulation may contain components such as phosphatidlycholine and cholesterol adapted to promote liposomal formation on mixing with an aqueous fluid but this has been demonstrated to be not essential for the binding of calcium. Generally, however, phosphatidylcholine will not comprise an effective amount of the phospholipid, except in instances where liposome formation is desired. The phospholipid formulation may also contain biologically active materials, as known in the art, including antibiotics and antithrombotic pharmaceuticals, It is possible to include an ionophore, but not necessary, as the examples below demonstrate improved osteointegration even in the absence of added ionophore.

The phospholipid coating is present at a concentration to improve, that is to say, to enhance, osteointegration. Preferred concentrations are in the range of 0.1 to 100 $\mu$mol/cm$^2$ particularly 1–10 $\mu$mol/cm$^2$.

The invention also relates to a method of making a prosthesis or implant having improved osteointegration, which method comprises providing a prosthesis or implant and coating a surface thereof with a phospholipid. The invention also relates to a method of surgery that comprises introducing a prosthesis or implant into a patient, the improvement which consists in coating a surface of the prosthesis or implant with a phospholipid at a concentration to improve osteointegration. Typically such methods comprise the step of treating the phospholipid coated prosthesis or implant with a simulated body fluid prior to use. In this specification the term "simulated body fluid" is taken to mean a fluid which has free calcium and phosphate ions which are generally provided in the form of calcium and phosphate salts.

The invention also relates to a prosthetic or implant kit.

The invention will be more clearly understood from the following description of some embodiments thereof, given by way of example only, with reference to the accompanying figures in which:

DETAILED DESCRIPTION OF THE INVENTION

The examples below are in vitro experiments using simulated body fluids described in the literature and whose composition is given in Examples 1 and 7. Various metal, ceramic and polymeric implant coupons have been coated with various phospholipid formulations. Upon incubation of these coated coupons in the Simulated Body Fluids, calcium phosphate deposition has been induced or enhanced. It is plausible that the same effect will occur in vivo and will result in improved osteointegration of an orthopaedic prosthesis or other implant.

EXAMPLE 1

Precipitation of Calcium Phosphate by Phospholipid-Containing Vesicles in an Aqueous Environment Method Thin films of excipients were produced on the surface of chromic acid cleaned round bottomed flasks from chloroform suspensions as well known to those skilled in the art. For the examples below, the following compositions were used:

Phosphatidylcholine:Phosphatidylserine:Cholesterol
Phosphatidylcholine:Phosphatidylinositol:Cholesterol
both at a molar ratio of 7:2:1
and
Phosphatidylcholine:Phosphatidylserine: Phosphatidylinositol: Cholesterol at a molar ratio of 7:1:1:1.

The thin films were resuspended in 2 mL of a Simulated Body Fluid[11] (71 mM NaCl; 5 mM KCl; 1.64 mM $Na_2HPO_4$; 2.36 mM $CaCl_2$ and 50 mM TES buffer, pH 7.2). The final volume was adjusted, using the same buffer to give an eight-fold dilution of the original chloroform suspension. Incubations were carried out in a shaking incubator set at 100 rpm and 37° C. in 12 mL polypropylene tubes. 1 mL samples were removed at daily intervals and washed three times in distilled water and fixed onto copper Transmission Electron Microscopy (TEM) grids using a 1:1 dilution with a 2% (v/v) solution of ammonium molybdate.

Results

TEM analysis of the samples demonstrated that for both the phosphatidylcholine:phosphatidylserine:cholesterol and phosphatidylcholine:phosphatidylinositol:cholesterol formulations, visible crystal-like structures were observed after 3 days incubation in the Simulated Body Fluid. For the phosphatidylcholine: phosphatidylserine:phosphatidylinositol:cholesterol formulation, crystal structures were observed after 7 days incubation.

Figure 1:
FIG. 1 shows a transmission Electron Micrograph of phosphatidylcholine:phosphatidylserine:cholesterol (7:2:1 molar ratio) incubation in Stimulated Body Fluid after 3 days incubation in shaking model at 37° C. demonstrating crystalline structures associated with the lamellar structures.

FIG. 1 shows a TEM micrograph of a sample from the phosphatidylcholine:phosphatidylserine:cholesterol incubation and clearly demonstrates the presence of crystalline structures in intimate contact with the multi-lamellar vesicles (large multi-layered liposomes).

EXAMPLE 2

Surface Coating of Implant Materials

Method

Two coating methodologies have been adopted for the surface coating of implant materials. These materials can be metal, ceramic or polymeric implant coupons. Examples of the following have been used in the Examples provided in this patent: three types of porous titanium oxide coupons (disks of diameter 13 mm and 26 mm; thickness 7 mm) were provided by a commercial supplier of implant prostheses; Ti-Pore300 (porous surface with average pore diameter of 40–80 μm), Ti-Pore600. (average pore diameter of 100 μm). and Ti-Pore300-HA (the above Ti-Pore300 coupons plasma sprayed with a layer of the ceramic hydroxyapatite (calcium phosphate)). Titanium coupons were obtained from another supplier (13 mm diameter; 6 mm thickness) that had a flat surface morphology. Polymeric materials were obtained form commercial suppliers and cast as known in the art to produce disks of implant material.

The first coating methodology involves the dissolving of the excipients in HPLC-grade chloroform. The formulations were applied either as 5 μL aliquots onto defined areas of the implant surface or as a greater volume to cover the entire implant surface. The chloroform quickly evaporates at room temperature, leaving the excipients in the form of a thin film.

The second coating methodology involves the production of a phospholipid suspension in an aqueous media. The phospholipid was weighed out and dissolved in 100 μL HPLC grade chloroform at a concentration of 222 μmol/mL. A thin film of phospholipid was produced on the wall of a glass round bottomed flask as described in Example 1. 1 mL of de-ionised water was then added stepwise to the flask and the flask shaken, resulting in a phospholipid suspension being produced. 40 μL of the phospholipid suspension was then gently layered onto a defined area of the material surface. The suspension was then dried onto the surface of the implant material by means such as air drying, freeze drying or rotary evaporation. This results in a thin film of phospholipid being deposited onto the surface of the material.

Results

The following spot sizes were produced on the Ti-Pore300 implant coupons. In the case of 444 μmol/ml solution, the spot concentration was estimated at 5 μmol/$cm^2$.

| Total Amount Excipients (μm/mL) | Spot Size Produced for phosphatidylserine formulation (mm) | Spot Size Produced for phosphatidylinositol formulation (mm) |
|---|---|---|
| 444 | 7 | 3 |
| 222 | 9 | 6.5 |
| 111 | 10 | 6 |
| 56 | 11 | 7 |

EXAMPLE 3

Induction of Calcium Phosphate Precipitation on the Surface of a Metal Surgical Implant using a Phospholipid Formulation Containing Phosphatidylserine Method The following excipients were weighed out:
Phosphatidylcholine=242.3 mg
Phosphatidylserine=70.2 mg
Cholesterol=17.1 mg TOTAL=329.6 mg (444 μmol)
(Molar Ratio 7:2:1)
and dissolved in 1 mL HPLC grade chloroform This solution was then used to undertake a serial dilution to produce standards at 444, 222, 111 and 56 μmol/mL chloroform. 5 μL of each of the 4 standards were then applied onto distinct areas of a clean titanium implant coupon—Ti-Pore300—(previously sonicated 3 times in HPLC grade chloroform for 30 minutes). The coupons were then placed in the incubation chamber and 10 mL of the Simulated Body Fluid described in Example 1 added. The samples were incubated at 37° C. for 7 days and daily visual checks undertaken.

Results

Figure 2:
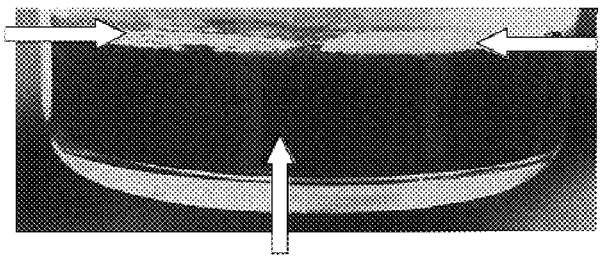
FIG. 2 shows a photograph of Ti-Pore300 surgical implant coupon surface coated with the phosphatidylcholine:phosphatidylserine:cholesterol (7:2:1 molar ratio) formulation after incubation in Simulated Body Fluid for 7 days at 37° C. demonstrating deposition of calcium phosphate on areas corresponding to where the formulation was applied.
Figure 3:
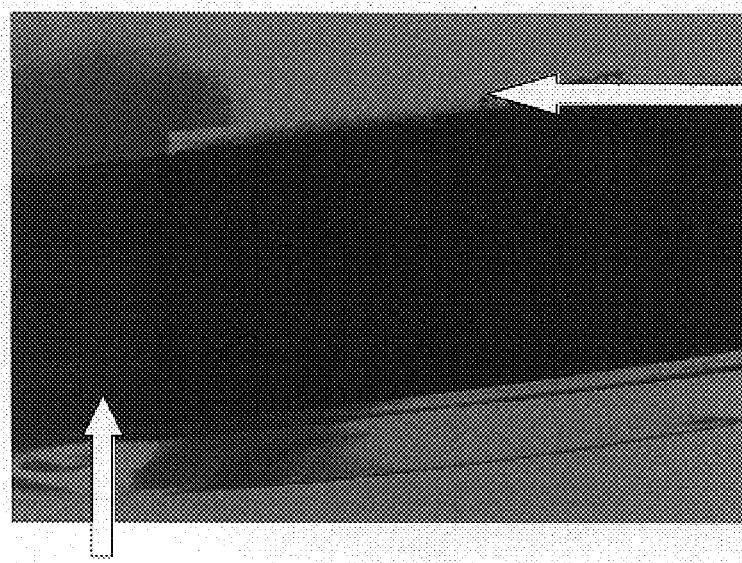
FIG. 3 shows a photograph of a side view of the Ti-Pore300 surgical implant coupon surface coated with the phosphatidylcholine:phosphatidylserine:cholesterol (7:2:1 molar ratio) formulation after incubation in Simulated Body Fluid for 7 days at 37° C. demonstrating deposition of calcium phosphate on area corresponding to where the formulation was applied.
Figure 4:
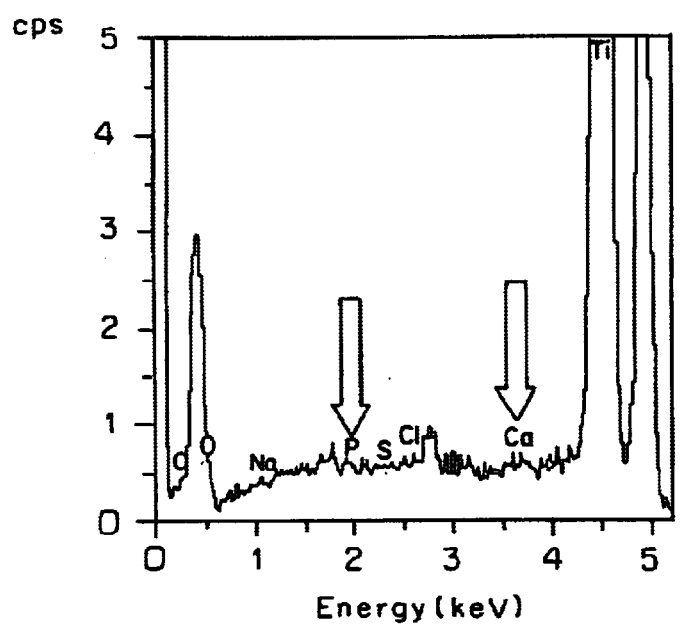
FIG. 4 shows SEM-EDAX analysis of the uncoated Ti-Pore300 surgical implant coupon surface after incubation in Simulated Body Fluid for 7 days at 37° C. demonstrating no peaks for calcium and phosphorus.
Figure 5:
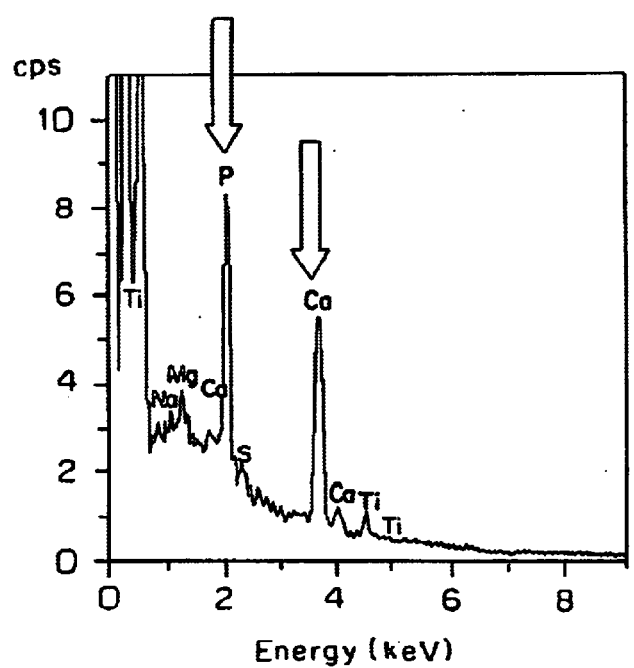
FIG. 5 shows SEM-EDAX analysis of the Ti-Pore300 surgical implant coupon surface coated with the phosphatidylcholine:phosphatidylserine:cholesterol (7:2:1 molar ratio) formulation at 444 $\mu$m/ml after incubation in Simulated Body Fluid for 7 days at 37° C. demonstrating significant peaks for calcium and phosphorus.

After two days incubation, white circles were visible on the titanium implant coupons at the points where the two highest excipient concentrations had been applied. The circle corresponding to the 444 μm/mL spot was approximately 1–2 mm in thickness at day 6. At day 7, photographs were taken of the titanium disc in situ prior to its removal from the incubation chamber. FIG. 2 is of the surface of the Ti-Pore300 implant coupon whilst FIG. 3 is a side on view of the 444 μm/mL coated spot. The implant coupons were rinsed 3 times in 10 mL of distilled water and placed in a drying oven at 60° C. for 18 hours. The surface of the implant coupon was then viewed by Scanning Electron Microscopy and subjected to elemental dispersive X-ray analysis (EDAX), without coating the implant coupon with palladium. FIG. 4 is an EDAX analysis undertaken on the uncoated Ti surface and demonstrates no calcium or phosphorus present. This indicates that the Ti surface itself does not act as a nucleating site for the precipitation of any significant amounts of calcium phosphate from the Simulated Body Fluid used. FIG. 5 is an EDAX analysis of the area coated with excipients at 444 μmol/mL. Significant peaks for calcium and phosphorous were observed. The calcium peak can only be due to the presence of the deposited calcium whilst the phosphorus peak may be partially due to the presence of the phospholipids. EDAX spot analysis was also undertaken on the area coated with excipients at 222 μmol/mL and calcium and phosphorus peaks were again detected, demonstrating that a range of excipient concentrations are capable of inducing calcium precipitation onto the implant surface.

Figure 6:
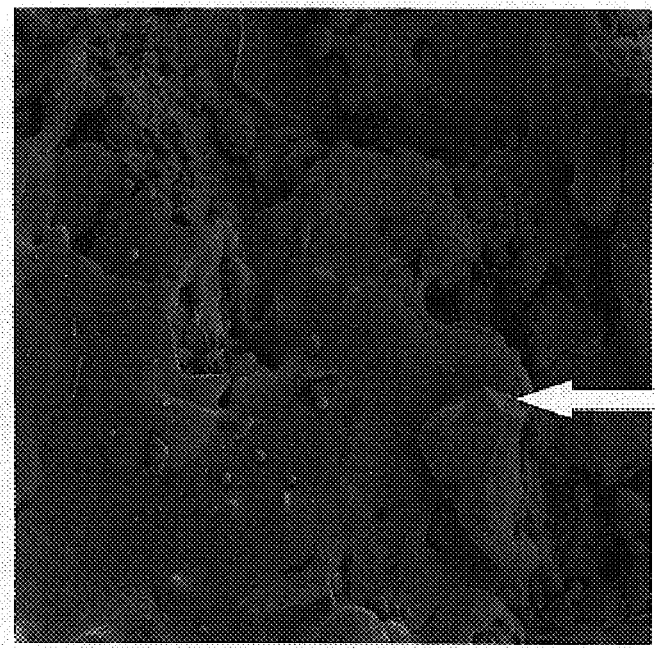
FIG. 6 shows SEM image of the Ti-Pore300 surgical implant coupon surface coated corresponding to the area coated with the phosphatidylcholine:phosphatidylserine:cholesterol (7:2:1 molar ratio) formulation at 444 $\mu$m/ml after incubation in Simulated Body Fluid for 7 days at 37° C. and after removal of phospholipid using chloroform demonstrating the smoothness of the implant surface.
Figure 7:
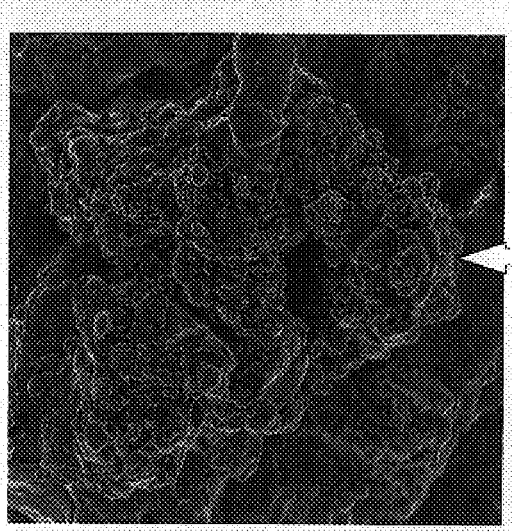
FIG. 7 shows SEM image of the uncoated Ti-Pore300 surgical implant coupon after incubation in Simulated Body Fluid for 7 days at 37° C. demonstrating a much rougher surface than in FIG. 6.
Figure 8:
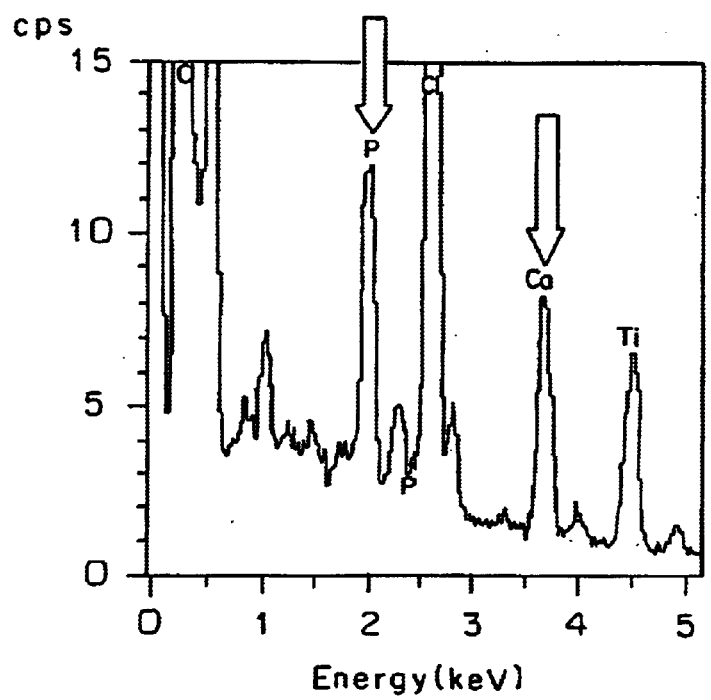
FIG. 8 shows SEM-EDAX analysis of the Ti-Pore300 surgical implant coupon surface corresponding to the area coated with the phosphatidylcholine:phosphatidylserine:cholesterol 7:2:1 molar ratio) formulation at 444 $\mu$m/ml after removal of phospholipid using chloroform demonstrating significant peaks for calcium and phosphorus.

The implant coupon was then washed three times using 20 mL HPLC-grade chloroform for 30 minutes in a sonicating waterbath to remove the phospholipid. This cleaning protocol has previously been shown to remove phospholipid from the surface of the Ti-Pore300 implant coupon. The implant coupon was then subjected to further Scanning Electron Microscopy analysis. FIG. 6 is a Scanning Electron Microscopy image of the surface previously coated with excipients at a concentration of 444 mmol/mL whilst FIG. 7 is of the uncoated Ti-Pore300 surface. The difference in morphology is particularly striking. EDAX analysis was undertaken (FIG. 8) and demonstrates that calcium and phosphorus peaks were still present. It should be noted that there is also a peak for carbon present in the EDAX analysis (FIG. 8) which suggests that some of the phospholipid may still be bound to the surface in association with the calcium deposit.

EXAMPLE 4

Induction of Calcium Phosphate Precipitation on the Surface of a Metal Surgical Implant using a Phospholipid Formulation Containing Phosphatidylinositol Method The following excipients were weighed out:
Phosphatidylcholine=242.3 mg
Phosphatidylinositol=76.3 mg
Cholesterol=17.1 mg
TOTAL=335.7 mg (444 μmol/mL)
(Molar Ratio 7:2:1)
and dissolved in 1 mL HPLC grade chloroform The experimental protocol used was as described in Example 3.

Results

Figure 9:
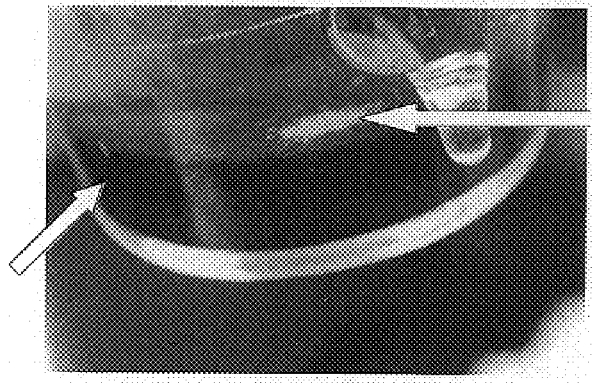
FIG. 9 shows a photograph of the Ti-Pore300 surgical implant coupon surface coated with the phosphatidylcholine:phosphatidylinositol:cholesterol (7:2:1 molar ratio) formulation after incubation in Simulated Body Fluid for 7 days at 37° C. demonstrating deposition of calcium phosphate on areas corresponding to where the formulation was applied.
Figure 10:
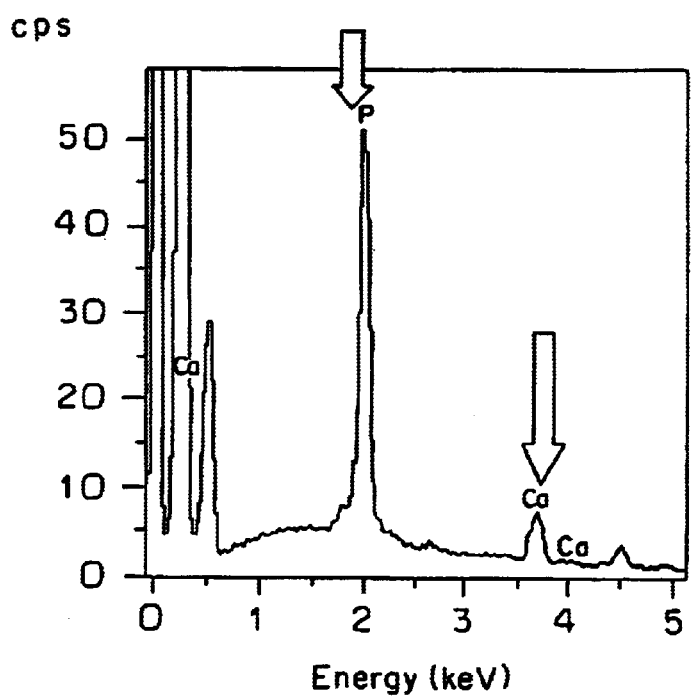
FIG. 10 shows SEM-EDAX analysis of the Ti-Pore300 surgical implant coupon surface coated with the phosphatidylcholine:phosphatidylinositol:cholesterol (7:2:1 molar ratio) formulation at 444 $\mu$m/ml after incubation in Simulated Body Fluid for 7 days at 37° C. demonstrating significant peaks for calcium and phosphorus.

At day 7, photographs were taken as in Example 3. FIG. 9 is of the Ti-Pore300 implant coupon coated with the formulation containing phosphatidylinositol with the area corresponding to the 444 and 222 μm/mL spots to the forefront. The implant coupon was rinsed and dried as in Example 3. The surface of the implant coupon was then viewed by Scanning Electron Microscopy and subjected to EDAX analysis. FIG. 10 is an EDAX analysis of the area coated with excipients at 444 μmol/mL and demonstrates that the phosphatidylinositol formulation is also capable of binding calcium to the surface of the implant coupon.

EXAMPLE 5

Induction of Calcium Phosphate Precipitation on the Surface of a Metal Surgical Implant using a Phospholipid Formulation of Phosphatidylserine Alone Method Phosphatidylserine was weighed out and dissolved in HPLC grade chloroform to give a final concentration of 222 μmol/mL. The experimental protocol used was as described in Example 3.

Results

The implant coupons were rinsed and dried as in Example 3. The surface of the implant coupon was then viewed by Scanning Electron Microscopy and subjected to EDAX analysis. EDAX analysis of the area coated with excipients at 222 μmol/mL demonstrated that phosphatidylserine alone is also capable of binding calcium to the surface of the implant coupon.

EXAMPLE 6

Induction of Calcium Phosphate Precipitation on the Surface of a Surgical Implant using a Formulation Containing Phosphatidylcholine Method The following excipients were weighed out:
Phosphatidylcholine=309 mg
Cholesterol=17.1 mg
TOTAL=326.1 mg (444 μmol)
and dissolved in 1 mL HPLC grade chloroform The experimental protocol used was as described in Example 3.

Results

Figure 11:
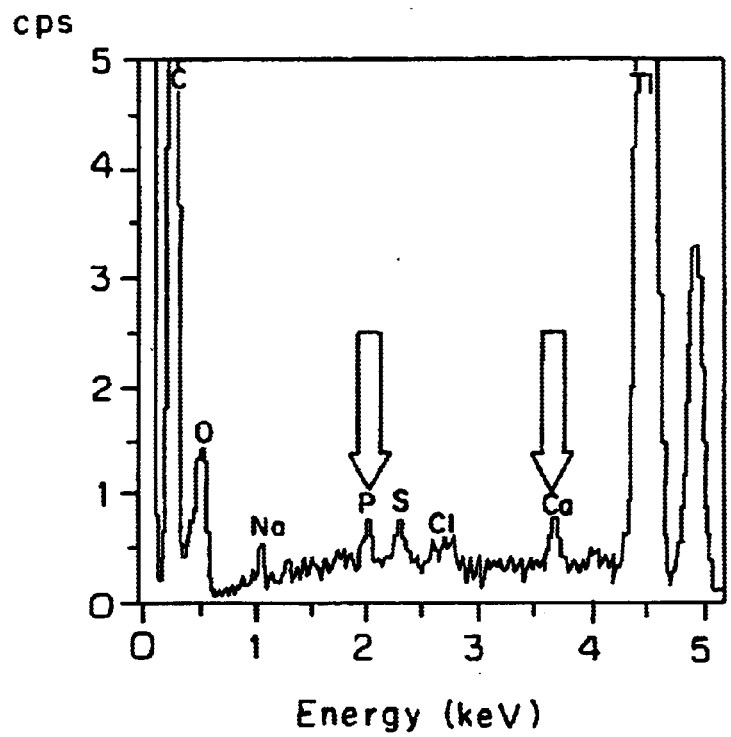
FIG. 11 shows SEM-EDAX analysis of the Ti-Pore300 surgical implant coupon surface coated with the phosphatidylcholine:cholesterol (9:1 molar ratio) formulation at 444 $\mu$m/ml after incubation in Simulated Body Fluid for 7 days at 37° C. demonstrating significant peaks for calcium and phosphorus.

After seven days incubation, a white circle became visible on the titanium implant coupon corresponding to where the excipients had been applied. The implant coupon was rinsed 3 times in 10 mL of distilled water and allowed to dry at room temperature for 4 days. FIG. 11 is an EDAX analysis of the area coated with excipients and demonstrates that the phosphatidylcholine formulation is also capable of binding calcium to the surface of the implant coupon after 7 days.

EXAMPLE 7

Induction of Calcium Phosphate Precipitation on the Surface of a Metal Surgical Implant using a Different Simulated Body Fluid Method The experimental procedure described in Example 5 was repeated using a different Simulated Body Fluid[12] (152 mM NaCl; 5 mM KCl; 1 mM $K_2HPO_4$; 1.5 mM $MgCl_2$; 27 mM $NaHCO_3$; 0.5 mM $Na_2SO_4$; 2.6 mM $CaCl_2$ and 50 mM Tris buffer at pH 7.4). This Simulated Body Fluid contains ions that are known to compete with calcium and phosphate in the precipitation of calcium phosphate in vivo.

Results

Similar results were obtained after 7 days incubation in this Simulated Body Fluid, demonstrating that the binding of calcium is not inhibited by the presence of competing divalent ions.

EXAMPLE 8

Induction of Calcium Phosphate Precipitation on Different Metal Surgical Implant Surfaces using a Phospholipid Formulation Containing Phosphatidylserine Method Ti-Pore600 implant coupons were coated with the phosphatidylserine formulation described in Example 3 at 444 μmol/mL and incubated in 10 mL Simulated Body Fluid at 37° C. Photographs of the incubation chamber were taken at day 0,1,2,3 and 7 and Scanning Electron Microscopy/EDAX analysis undertaken after 9 days incubation, again without coating the implant coupon with palladium.

Results

Figure 12:
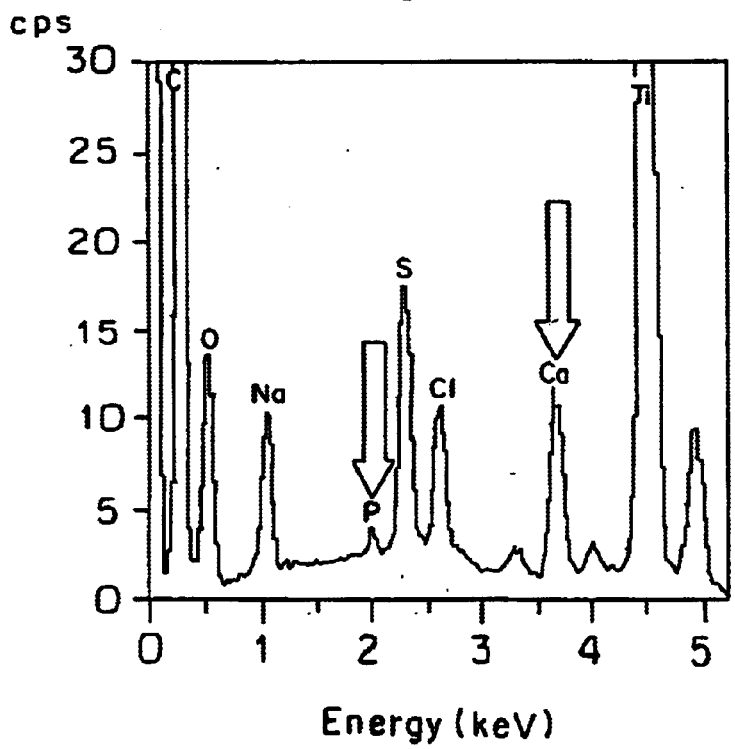
FIG. 12 shows SEM-EDAX analysis of the Ti-Pore600 surgical implant coupon surface coated with the phosphatidylcholine:phosphatidylserine:cholesterol (7:2:1 molar ratio) formulation at 444 m/ml after incubation in Simulated Body Fluid for 9 days at 37° C. demonstrating significant peaks for calcium and phosphorus.

After only a few hours incubation, white circles corresponding to where the phospholipid formulation had been applied were visible. After 9 days incubation, the implant coupon was washed and dried as in Example 5. EDAX analysis did not detect any significant amounts of calcium or phosphorous on the uncoated surface as was the case for the Ti-Pore300 implant coupon. FIG. 12 is an EDAX analysis of the area coated with excipients and demonstrates that the formulation is capable of binding calcium to the surface of different implant coupons.

EXAMPLE 9

Induction of Calcium Phosphate Precipitation on Different Metal Implant Surfaces using a Formulation Containing Phosphatidylserine Only Method Smooth titanium coupons were coated with phosphatidylserine only as described in Example 5 at 222 μmol/mL. The experimental protocol used was as described in Example 3.

Results

Figure 13:
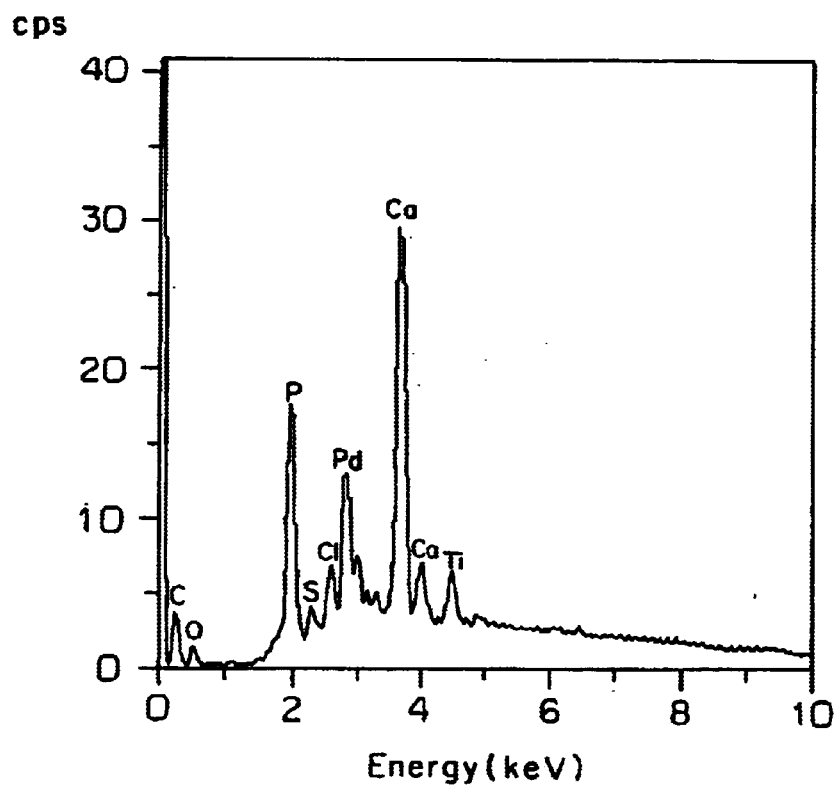
FIG. 13 shows a SEM-EDAX analysis of the smooth titanium coupon surface, coated with phosphatidylserine after incubation in Simulated Body Fluid for 7 days at 37° C. demonstrating significant peaks for calcium and phosphorus.

After only a few minutes incubation, white circles corresponding to where the phospholipid formulation had been applied were visible. FIG. 13 is an EDAX analysis of the area coated with excipients and demonstrates that the formulation is capable of binding calcium to the surface of different implant coupons.

EXAMPLE 10

Induction of Calcium Phosphate Precipitation on Ceramic Surgical Implant Surfaces using a Formulation Containing Phosphatidylserine Method Ti-Pore300-HA implant coupons were coated with the phosphatidylserine formulation at 444 μmol/mL as described in Example 3 and incubated in 10 mL Simulated Body Fluid at 37° C. Photographs were taken at day 0,1,2,3 and 7.

Results

Figure 14:
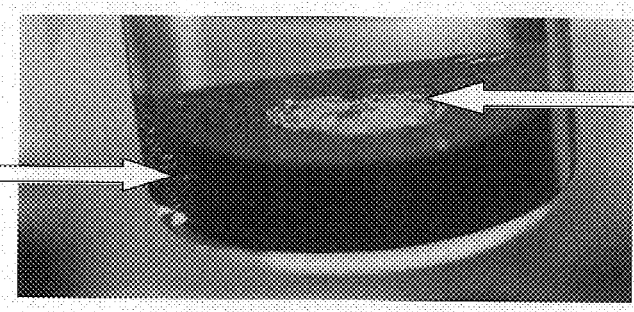
FIG. 14 shows a photograph of the Ti-Pore300-HA surgical implant coupon surface, coated with phosphatidylcholine:phosphatidylserine:cholesterol (7:2:1 molar ratio) formulation after 2 hours incubation in Simulated Body Fluid at 37° C. demonstrating deposition of calcium phosphate on the area corresponding to where the formulation was applied.

After only a few hours incubation, white circles corresponding to where the phospholipid formulation had been applied were visible. FIG. 14 is the surface of the Ti-Pore300-HA implant coupon after incubation for 2 hours in Simulated Body Fluid demonstrating that a similar matrix can be formed on a ceramic surface.

EXAMPLE 11

Induction of Calcium Phosphate Precipitation on a Polymeric Implant Surface using a Formulation Containing Phosphatidylserine Only Method Polymeric films of poly(methyl methacrylate) (PMMA) were cast using techniques well known to those skilled in the art. The smooth polymeric films were then coated with a phosphatidylserine suspension in an aqueous medium as described in Example 2 and incubations set up and analysed as described in Example 8.

Results

Figure 15:
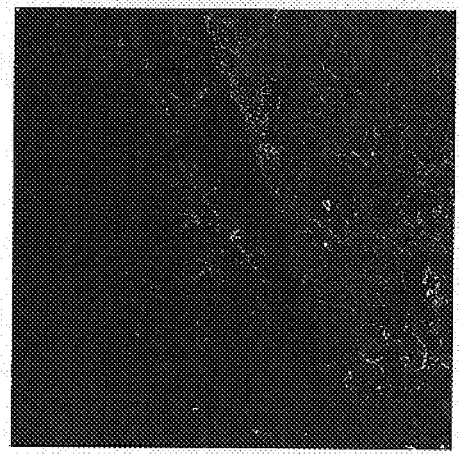
FIG. 15 shows a SEM image of a poly (methylmethacrylate) sheet coated with phosphatidylserine.
Figure 16:
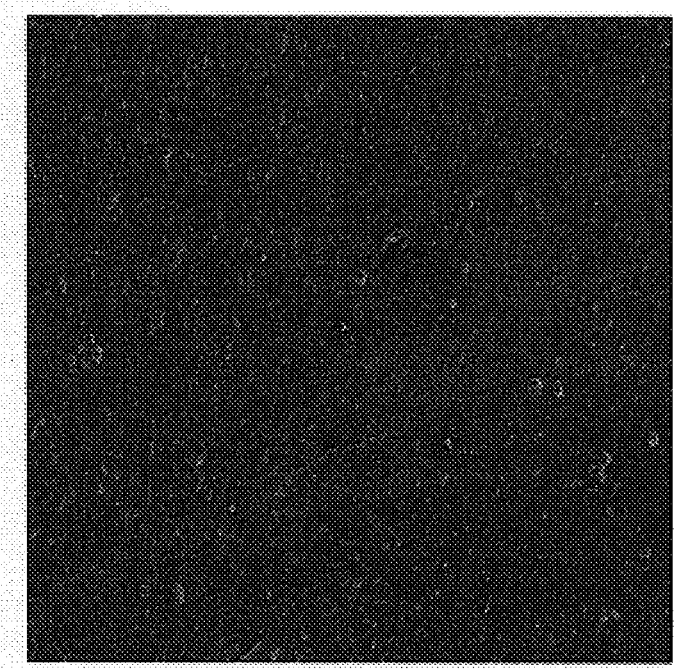
FIG. 16 shows a SEM image of a poly (methylmethacrylate) sheet coated with phosphatidylserine after 7 days incubation in Simulated Body Fluid at 37° C.

Scanning Electron Microscopic analysis of the phospholipid coated poly(methyl methacrylate) films demonstrated a continuous thin coating on the surface (FIG. 15) prior to incubation in Simulated Body Fluid. After incubation in Simulated Body Fluid for 7 days, the Scanning Electron Microscopic analysis demonstrated a that the coating of phospholipid had mineralised (FIG. 16) and Scanning Electron Microscopy-EDAX analysis demonstrated the presence of calcium and phosphate crystals. Surface mapping of the sample was also undertaken using Scanning Electron Microscopy-EDAX analysis and it was found that the areas of the surface containing calcium and phosphate corresponded to the areas of the surface containing carbon, demonstrating that the calcium is associated with the areas of the polymer coated with phospholipid.

EXAMPLE 12

Induction of Calcium Phosphate Precipitation on a Metal Surgical Implant Surface Coated with a Formulation Containing Phosphatidylserine, Conditioned by Incubation in Serum Method A Ti-Pore300 implant coupon was coated with the phosphatidylserine formulation as described in Example 3. The implant coupon was then incubated for 1 hour in commercially available human serum at 37° C., washed twice with 20 mL and then incubated in Simulated Body Fluid as described in Example 4. Scanning Electron Microscopy/EDAX analysis was then undertaken after 9 days incubation, again without coating the implant coupon with palladium.

Results

Figure 17:
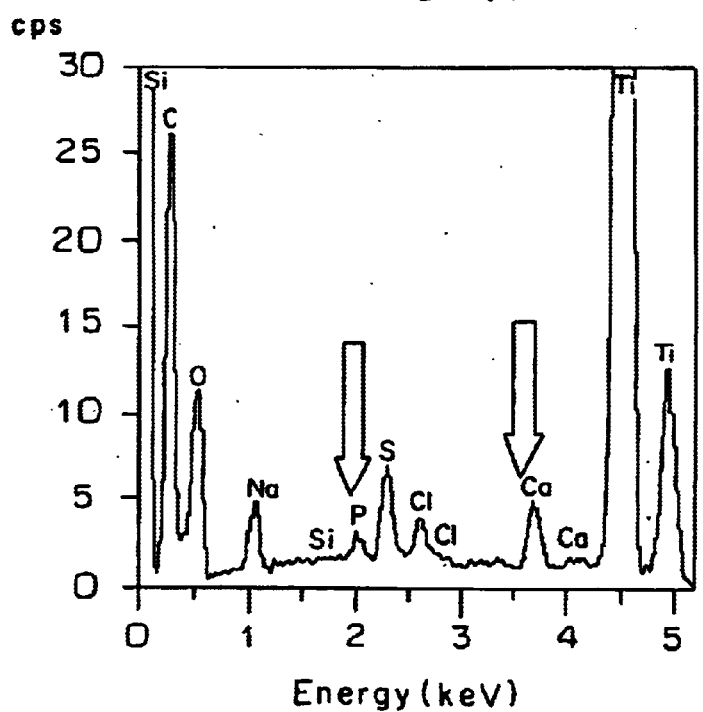
FIG. 17 SEM-EDAX analysis of the Ti-Pore300 surgical implant coupon surface coated with the phosphatidylcholine:phosphatidylserine:cholesterol (7:2:1 molar ratio) formulation at 222 μm/ml after conditioning with serum proteins for 1 hour followed by incubation in Simulated Body Fluid for 9 days at 37° C. demonstrating significant peaks for calcium and phosphorus.

After approximately 30 minutes incubation in the Simulated Body Fluid, a white circle corresponding to where the phospholipid formulation had been applied was visible. EDAX analysis of the area coated with excipients (FIG. 17) demonstrated that even in the presence of a conditioning layer of serum proteins, the formulation is capable of binding calcium to the surface of the implant coupon.

The invention is not limited to the embodiments hereinbefore described which may be varied in both construction and detail.

REFERENCES

1. Soballe K., Fiedman R. J. (1996) Calcium hydroxyapatite in total joint arthroplasty. In: Human Biomaterial Applications (Eds. D. L. Wise, D. J. Tarantolo, D. E. Altobalti, M. J. Yaszemuki, J. D. Gresser) Humana Press Inc. New Jersey, pp137–167
2. Revell, P. A. (1982) Tissue reactions to joint prostheses and the products of wear and corrosion. Current Topics pathology 71:73–102
3. Dhert, W. J. A.(1994) Retrieval studies on calcium phosphate-coated implants. Medical Progress through Technology 20:143–154

4. Anthony, P. P., Gie, G. A., Howie, C. R. & Ling, R. S. (1990) Localised endosteal bone lysis in relation to soundly fixed femoral components of cemented total hip replacements: a possible mechanism. J. Bone Jt. Surg. 72B:971–979
5. Lewis G. (1997) Properties of acrylic bone cement: State of the art review. J.Biomed.Mater.Res. 38:155–182.
6. Skrtic, D. & Eanes, ED. Membrane-mediated precipitation of calcium phosphate in model liposomes with matrix vesicle-like lipid composition. Bone Miner. (1992) 16:109–119.
7. Eanes, ED. & Hailer, AW. Liposome-mediated calcium phosphate formation in metastable solutions. Calcified Tissue International (1985) 37:390–394.
8. Heywood, BR. & Eanes, ED. An ultrastructural study of calcium phosphate formation in multilamellar liposome suspensions. Calcified Tissue International (1987) 41:192–201.
9. Eanes, ED., Hailer, AW. & Costa, JL. Calcium phosphate formation in aqueous suspensions of multilamellar liposomes. Calcified Tissue International (1984) 36:421–430.
10. Eanes, ED. & Hailer, AW. Calcium phosphate precipitation in aqueous suspensions of phosphatidylserine-containing anionic liposomes. Calcified Tissue International (1987) 40:43–48.
11. Vogel, J. J. (1986) Calcium-phosphate solid-phase induction by dioleoylphosphatidate liposomes. J.Colloid and Interface Science 111:152–159
12. Radin, S & Ducheyne, P.(1996) Effect of serum proteins on solution-induced surface transformations of bioactive ceramicS. J Biomedical Materials Research 30:273–279.

What is claimed is:

1. A prosthesis or implant adapted to be implanted within a human or animal body, and having a surface adapted to contact bone within said human or animal body, wherein said surface is coated directly with a phospholipid or mixture of phospholipids in an amount sufficient to provide improved osteointegration of the prosthesis or implant by inducing the precipitation of calcium phosphate on the surface of the said prosthesis or implant.

2. The prosthesis or implant of claim 1, wherein the phospholipid is a negatively charged phospholipid.

3. The prosthesis or implant of claim 2, wherein the negatively charged phospholipid is phosphatidylserine or phosphatidylinositol or a mixture thereof.

4. The prosthesis or implant of claim 1, wherein the amount sufficient is a concentration in the range of 0.1–100 $\mu$mol/cm$^2$.

5. The prosthesis or implant of claim 4, wherein the amount sufficient is a concentration in the range of 0.1–10 $\mu$mol/cm$^2$.

6. The prosthesis or implant of any one of claims 1 to 5, wherein the surface is smooth, rough or porous.

7. The prosthesis or implant of claim 6, wherein the surface is metal, ceramic or polymeric.

8. The prosthesis or implant according to claim 1 in which the phospholipid primarily coats only parts of the surface of the prosthesis or implant that is likely to be subject to mechanical stress in vivo.

9. The prosthesis or implant according to claim 1 in which the phospholipid is substantially free of effective amounts of phosphatidylcholine.

10. The prosthesis or implant according to claim 1 wherein said surface comprises calcium phosphate.

11. The prosthesis or implant according to claim 1 in which the phospholipid coating further comprises a biologically active material.

12. The prosthesis or implant of claim 11, wherein said biologically active material is at least one antibiotic, antithrombotic or mixture thereof.

13. A method of making a prosthesis or implant having improved osteointegration, which method comprises providing a prosthesis or implant adapted to be implanted within a human or animal body, and having a surface adapted to contact bone within said human or animal body, and coating said surface thereof directly with a phospholipid or mixture of phospholipids in an amount sufficient to provide improved osteointegration of the prosthesis or implant by inducing the precipitation of calcium phosphate on the surface of the said prosthesis or implant.

14. In a method for implanting a prosthesis or implant in a human or animal body adjacent or in contact with a bone, the improvement wherein said prosthesis or implant has a surface coated directly with a phospholipid or mixture of phospholipids in an amount sufficient to provide improved osteointegration of the prosthesis or implant by inducing the precipitation of calcium phosphate on the surface of said prosthesis or implant, and said coated surface is placed adjacent or in contact with said bone.

15. A method as claimed in claims 13 or 14 in which the phospholipid comprises a phospholipid suspension which is lyophilised or otherwise dried onto the surface of the prosthesis or implant.

16. A method as claimed in claims 13 or 14 in which the phospholipid coating is applied primarily to parts of the surface of the prosthetic or implant that are likely to be subject to mechanical stress in vivo.

17. A method as claimed in claims 13 or 14 in which the phospholipid coated prosthesis or implant is treated with a simulated body fluid prior to use.

18. The prosthesis or implant of claim 1 or the method according to claim 13 or 14, wherein the prosthesis or implant is an orthopaedic, dental or load-bearing prosthesis or implant.

* * * * *